(12) United States Patent
Griffith et al.

(10) Patent No.: US 9,381,338 B2
(45) Date of Patent: Jul. 5, 2016

(54) MEDICAL CONNECTOR WITH A REVERSIBLY DEFORMABLE LOBE

(71) Applicant: AVENT, INC., Alpharetta, GA (US)

(72) Inventors: Nathan C. Griffith, Roswell, GA (US); Donald J. McMichael, Roswell, GA (US); John A. Rotella, Roswell, GA (US); Scott M. Teixeira, Cumming, GA (US)

(73) Assignee: Avent, Inc., Alpharetta, GA (US)

( * ) Notice: Subject to any disclaimer, the term of this patent is extended or adjusted under 35 U.S.C. 154(b) by 633 days.

(21) Appl. No.: 13/690,870

(22) Filed: Nov. 30, 2012

(65) Prior Publication Data

US 2014/0155866 A1    Jun. 5, 2014

(51) Int. Cl.
*A61M 39/10*    (2006.01)
*A61J 15/00*    (2006.01)

(52) U.S. Cl.
CPC ........ *A61M 39/1011* (2013.01); *A61J 15/0015* (2013.01); *A61J 15/0092* (2013.01); *A61M 39/10* (2013.01); *A61J 1/1481* (2015.05); *A61J 15/0069* (2013.01)

(58) Field of Classification Search
CPC . A61J 15/0015; A61J 15/0092; A61J 1/1418; A61J 1/1481; A61M 39/10; A61M 39/1011
USPC ........................................................ 604/533
See application file for complete search history.

(56) References Cited

U.S. PATENT DOCUMENTS

| | | | |
|---|---|---|---|
| 5,836,924 A | 11/1998 | Kelliher et al. | |
| 6,458,106 B1 | 10/2002 | Meier et al. | |
| 6,736,797 B1 | 5/2004 | Larsen et al. | |
| 6,802,836 B2 | 10/2004 | Bouphavichith et al. | |
| 6,976,980 B2 | 12/2005 | Brenner et al. | |
| 6,979,322 B2 | 12/2005 | Chu et al. | |
| 2005/0101910 A1 | 5/2005 | Bowman et al. | |
| 2005/0107743 A1 | 5/2005 | Fangrow, Jr. | |
| 2006/0100604 A1 | 5/2006 | Brenner et al. | |
| 2006/0129090 A1 | 6/2006 | Moberg et al. | |
| 2007/0112323 A1* | 5/2007 | Daly | 604/411 |
| 2007/0185441 A1* | 8/2007 | Fangrow, Jr. | 604/93.01 |
| 2008/0183153 A1 | 7/2008 | Enns | |

(Continued)

FOREIGN PATENT DOCUMENTS

EP          0 315 423 A1    5/1989
WO        WO 96/36378 A1    11/1996

(Continued)

*Primary Examiner* — Kevin C Sirmons
*Assistant Examiner* — Deanna K Hall
(74) *Attorney, Agent, or Firm* — Dority & Manning, P.A.

(57) ABSTRACT

A connector for coupling to a base of medical device equipped with a circular hub having a circumferential recess. The connector includes a cap having a top surface, a bottom surface, a central region, and a circumferential region. The cap defines at least two slots extending from the circumferential region towards the central region, the slots defining the cap into at least one lobe. The at least one lobe has an outward projecting lift tab and an inward projecting catch. Positioning the connector on the circular hub and depressing the connector engage the catch with the circumferential recess of the circular hub so the connector can rotate completely about the circular hub. Lifting the one lift tab to reversibly displace the lobe and its respective catch radially to disengage from the circumferential recess decouples the connector.

11 Claims, 10 Drawing Sheets

(56) References Cited

U.S. PATENT DOCUMENTS

2008/0243085 A1 10/2008 Destefano
2010/0076383 A1 3/2010 Bouphavichith et al.
2010/0185159 A1 7/2010 Bagwell et al.
2012/0029483 A1 2/2012 Griffith et al.

FOREIGN PATENT DOCUMENTS

| WO | WO 98/58693 A1 | 12/1998 |
| WO | WO 2004/091692 A2 | 10/2004 |
| WO | WO 2008/114220 A2 | 9/2008 |
| WO | WO 2010/029853 A1 | 3/2010 |

* cited by examiner

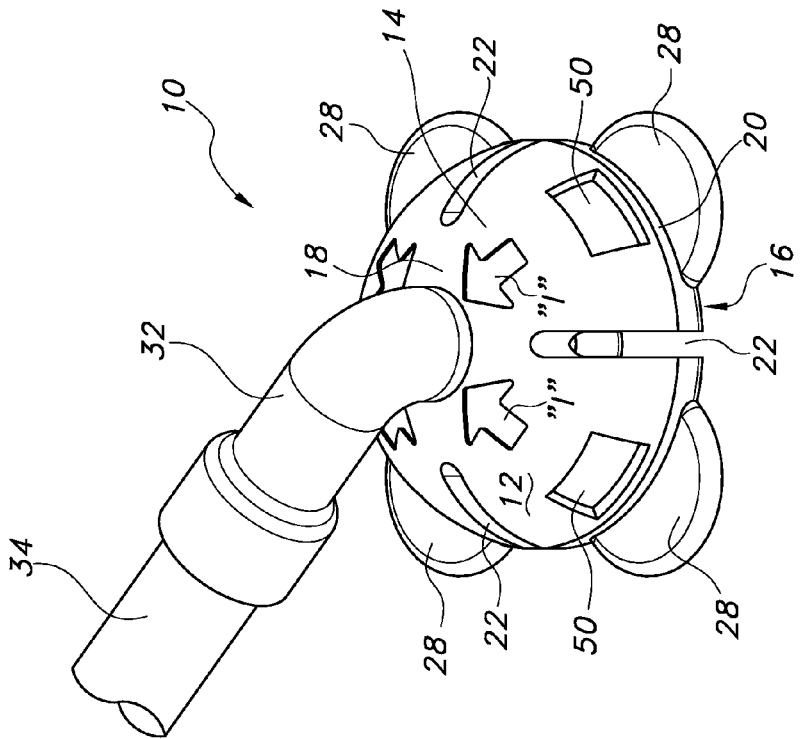
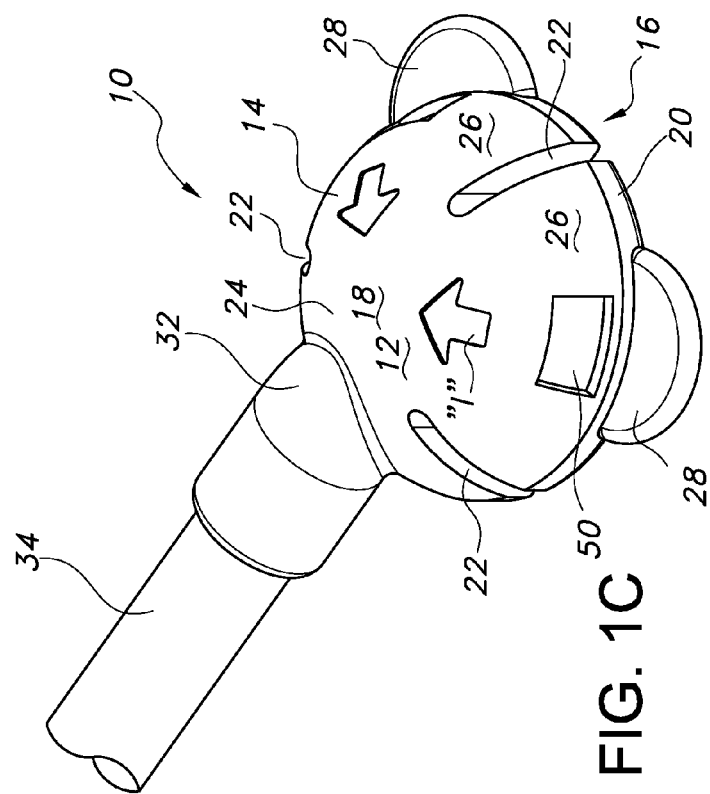
FIG. 1D
FIG. 1C

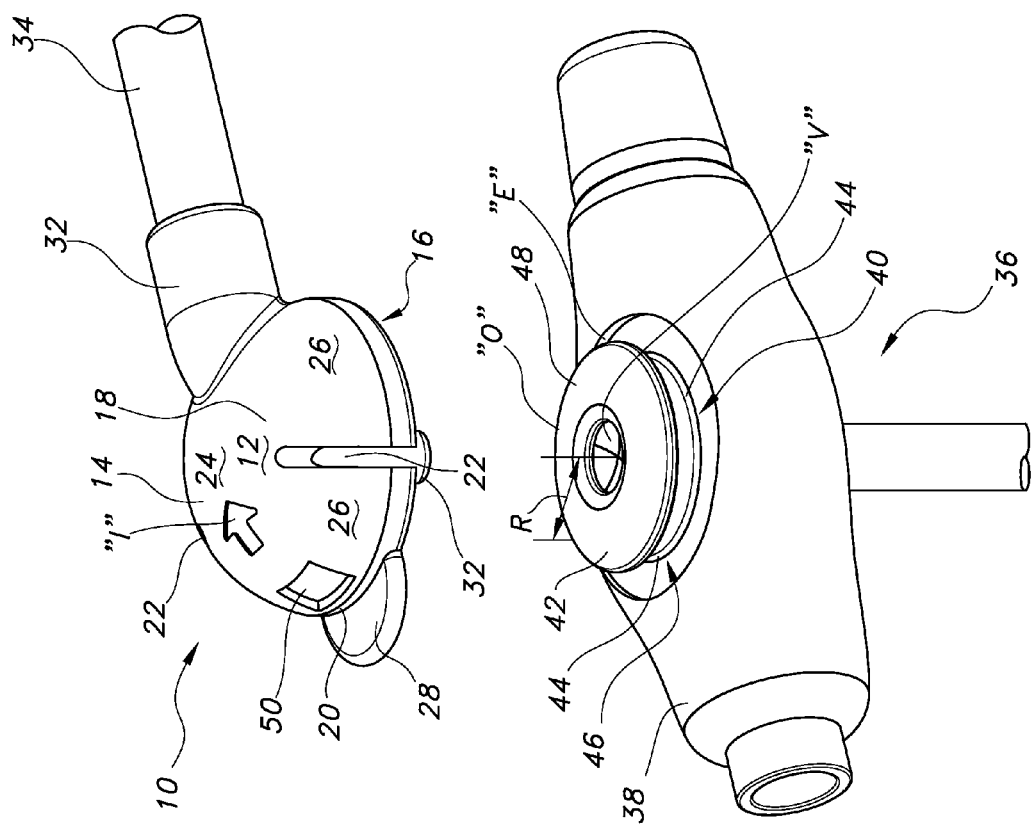

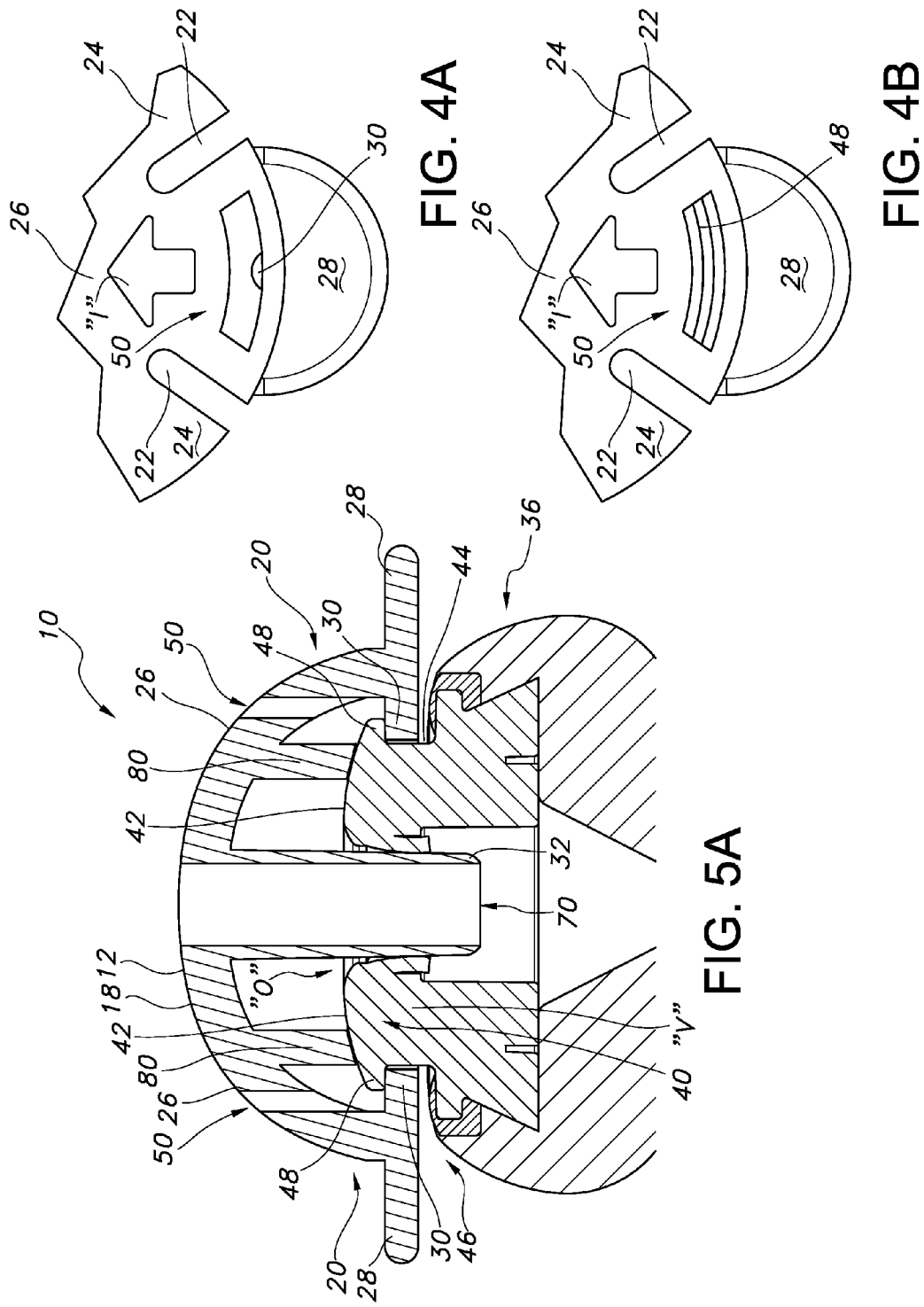

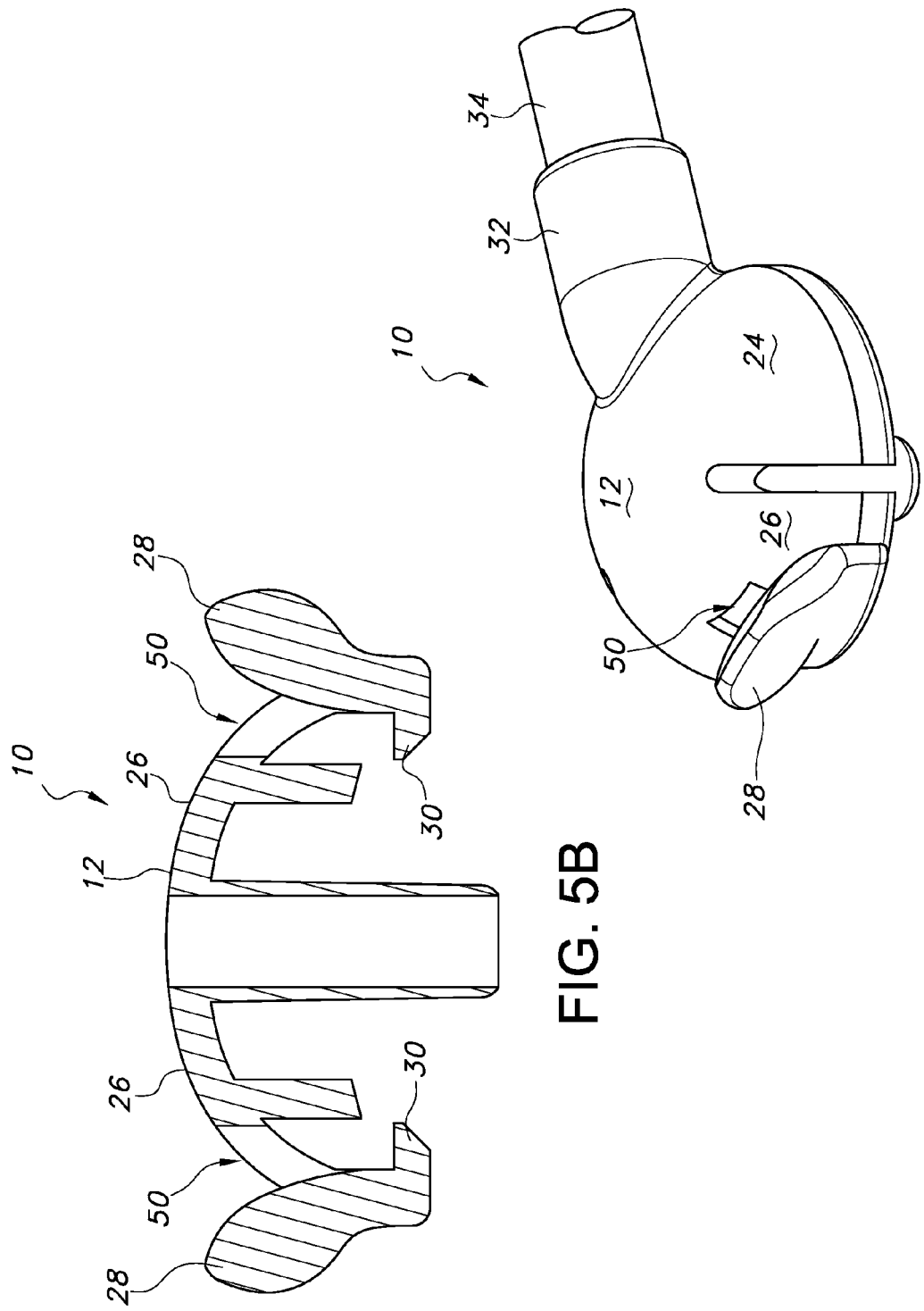

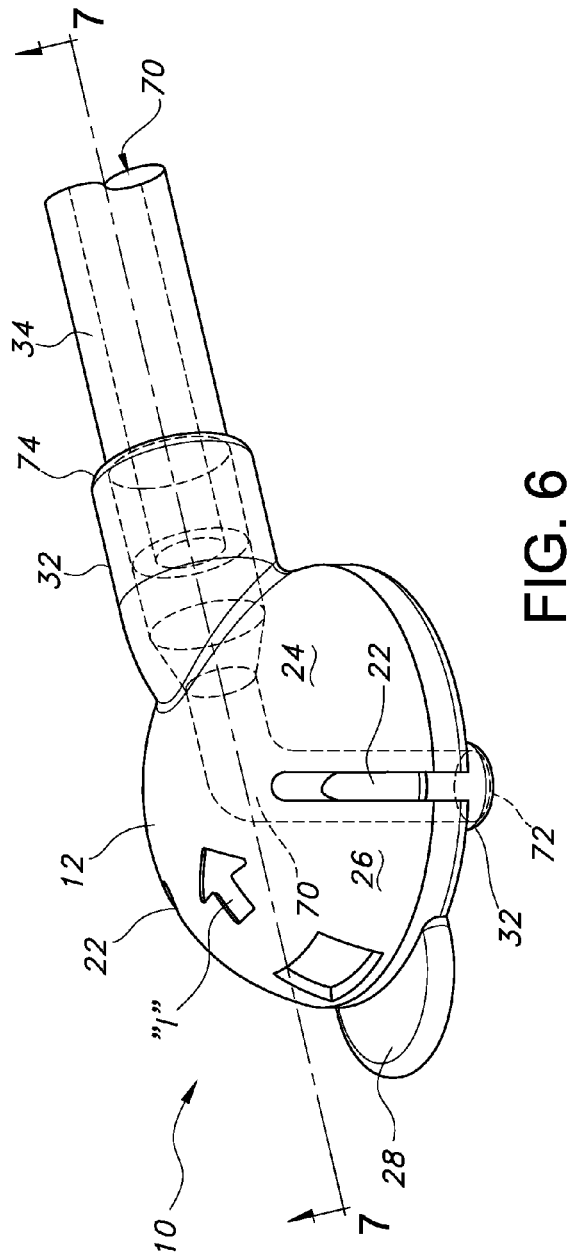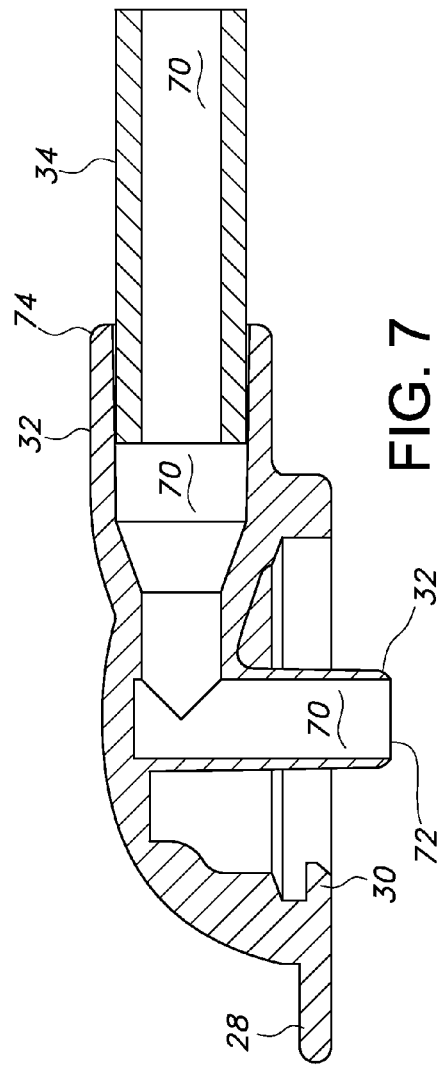

MEDICAL CONNECTOR WITH A REVERSIBLY DEFORMABLE LOBE

FIELD OF THE INVENTION

The present invention relates to improved connectors that convey fluids from a supply tube to an indwelling catheter. More particularly, it relates to an extension set with a particular connector which joins to an enteral feeding device.

BACKGROUND

Numerous situations exist in which a body cavity needs to be catheterized to achieve a desired medical goal. One relatively common situation is to provide nutritional solutions or medicines directly into the stomach or intestines. A stoma is formed in the stomach or intestinal wall and a catheter is placed through the stoma. This surgical opening and/or the procedure to create the opening is common referred to as "gastrostomy". Feeding solutions can be injected through the catheter to provide nutrients directly to the stomach or intestines (known as enteral feeding). A variety of enteral feeding devices have been developed over the years, including some having a "low profile" exterior portion which sits on a patient's skin, as well as those having the more traditional or non-low profile configurations. These enteral feeding devices are also known as "percutaneous transconduit catheters", "percutaneous transconduit tubes", "gastrostomy catheters", "percutaneous gastrostomy catheters", "PEG catheters" or "enteral feeding catheters". U.S. Pat. No. 6,019,746 for a "Low Profile Balloon Feeding Device" issued to Picha et al. on Feb. 1, 2000, provides an example of one device.

An enteral feeding device serves as the pathway through the stoma for transconduit of feeding solution into the stomach or intestine. During feeding, the enteral feeding device must be connected to a tube that is associated with a pressurizing source, e.g. pump, that generates pressure to drive feeding solution from a reservoir through the tube and into and through the enteral feeding device into the stomach or intestine. Feeding may take several hours and may occur at night while a patient is sleeping. Maintaining a robust and leak proof connection between the tube and the enteral feeding device is important. It is also very desirable that the connection withstand twisting, torquing and pulling forces generated by movement of a patient.

However, a problem universal to low profile and non-low profile enteral feeding devices is the difficulty in connecting and disconnecting the locking adapter of the tube to and from the enteral feeding device base or head. Many prior art enteral feeding devices have a low profile base and an indwelling catheter which extends from the base. A distal end of the catheter of such a device/assembly often includes a balloon which may be expanded to hold the catheter in a position in a body lumen, such as a stomach lumen.

An enteral feeding device often uses a plug to occlude the feeding passage opening in the base. This plug is attached to the device by a tether. Prior to connecting an extension set to such a conventional enteral feeding device, the step of removing the plug from the base to allow access to the feeding passage opening is required.

Other conventional enteral feeding devices are designed with a base or "head" having a locking cover member in the feeding passage opening to an indwelling catheter. The locking cover member is configured to receive an adapter as the connector, which may be connected to the end of the tube. Generally speaking, these locking cover members have a keyway, a groove, and a stop member and they incorporate a slot to provide a design that is similar to the female portion of a bayonet fitting. An adapter that fits into the locking cover member has a dispensing projection and a key portion attached to that projection. The adapter is pushed into the locking cover member and twisted in place until it interlocks. Exemplary illustrations of these conventional features may be found in the above referenced U.S. Pat. No. 6,019,746.

Connecting, changing and/or disconnecting a tube having an interlocking adapter to/from a locking cover member like that of U.S. Pat. No. 6,019,746 can be a surprisingly difficult. When visibility of the base of the enteral feeding device is limited, e.g. if the patient is overweight, if it is dark, aligning and maneuvering the interlocking adapter in or out of the base must rely on touch only. If the patient has impaired motor skills, fitting an interlock adapter in the locking cover member presents challenges during the positioning, pushing and twisting steps. Yet, without being sure that the adapter is correctly connected to the device, there is a risk of leaking gastric contents and or feeding solution onto a patient's skin surface, clothing, and the like. Further, when the adaptor sits tightly within the base, it may be difficult to remove, thereby requiring extensive pulling, movement of the connected extensions set and base and even unwanted displacement of the base, all of which can cause leakage or irritate a sensitive stoma site.

Some conventional interlocking adapters are configured to allow partial rotation within the base after the adapter has been fitted in place. That is, after the inserted interlocking adapter in the locking cover member is twisted so the key portion travels past a "detent", the interlocking adapter can rotate between a position where the key portion contacts a stop and a position where the key portion contacts a detent. Unfortunately, the limited range of motion allows the interlocking adapter to transmit torquing force to the enteral feeding catheter. This transfer of force may cause the catheter to twist or pull which can cause leakage or irritate a sensitive stoma site. If sufficient force is inadvertently encountered, the key portion of the interlocking adapter may be forced past the detent as it would be when a patient or care give is disconnecting the locking adapter. After the key portion is forced past the detent, it can readily align with the slot/keyway thereby allowing the extension set to inadvertently become completely disconnected.

These conventional connectors have evident drawbacks that remain unresolved.

The popularity of enteral feeding devices having low profile heads or bases has also resulted in a conversion kit that provides a low-profile base or head component that is clamped onto a percutaneously inserted catheter (i.e., catheter tubing) that is inserted through the abdominal wall to a patient's stomach. Such a low-profile conversion kit is described in U.S. Pat. No. 5,549,657. According to that patent, base or head component has an anti-reflux valve assembly and a two-part clamp. After the base or head component is clamped on the end of a catheter, it functions as the base or head for the catheter. The anti-reflux valve assembly includes a circular seat. A recess located beneath the seat is configured to receive opposed lips of a snap-fit tube connector that snaps onto the circular seat. An example of such a low-profile conversion kit is commercially available as the Gaurderer Genie™ PEG System Kit available from Bard Nordic (Helsingborg, Sweden), a subsidiary of C.R. Bard Inc.

When a patient is ready to be fed, a snap-type tube connector is snap fitted onto the anti-reflux valve assembly by pressing the snap-type tube connector against the anti-reflux valve assembly to urge the lips of the tube connector over the circular seat and into the recess located beneath the circular seat. When feeding is complete, the snap-type tube connector is removed by prying or pulling on a set of opposed, reinforced ears. Attachment and detachment of the tube connector is facilitated by a set of opposed slots that enhances axial and radial distortion and flexure of only the central portion of the snap-type connector when a force is applied to one or both of the opposed ears.

Connecting, changing and/or disconnecting a snap-type connector to/from such a low-profile enteral feeding head or base may also be a surprisingly difficult exercise at least for the same reasons as conventional interlocking adapter. Moreover, the application of force to press the snap-type connector onto the head and also to pry it off the head transfers forces directly to the enteral feeding device which may create discomfort and cause irritation to the sensitive stoma site. The low-profile of the head and its relatively small size (e.g., typically between about 13 mm and 25 mm in diameter) also creates difficulty in that opposed ears of the snap-type connector can extend over the ends of the head and lie adjacent or even against the skin of the patient to make it difficult to grasp or pinch the ears between the fingers.

Accordingly, there is a need for a connector for coupling a medical fluid supply tube to the head of a catheter device having a circular hub. For example, there is a need for an enteral feeding extension set connector which permits a user or health care provider to easily connect and disconnect an extension set to the base of an enteral feeding device. Such a system would permit a user or health care provider to easily and reliably disconnect the previous, used, connector and connect a new connector, desirably without needing to see the base.

SUMMARY

In response to the difficulties and problems discussed herein, the present invention provides a connector for coupling a medical fluid supply tube ("the tube") to a base of a catheter device (e.g., an enteral feeding device) when the base is equipped with a circular hub having a radius, a top surface, a side surface, and a circumferential recess defined in the side surface.

The connector is composed of a cap having a top surface, a bottom surface, a central region, and a circumferential region. The cap defines at least two slots, each slot extending from the circumferential region of the cap towards the central region, the slots defining at least one lobe that is made of a resilient material or at least has a resilient portion. The at least one lobe includes a circumferential region and a bottom surface that respectively coincide with a parts of the circumferential region and bottom surface of the cap, a lift tab at the circumferential region that projects outward from the top surface, and a catch projecting inward from the bottom surface. The catch is configured to releasably engage the circumferential recess defined in the side surface of the circular hub. The connector is coupled to the circular hub by positioning the connector on the circular hub and pressing the connector downwards (i.e., towards the enteral feeding device) until the catch (or catches) engage the circumferential recess defined in the side surface of the circular hub. The connector decouples from the circular hub by lifting (or in some embodiments squeezing) the lift tab(s) to extend the circumferential region of the lobe sufficiently away from the central region of the cap and the circular hub so that the respective catch of the lobe disengages from the circumferential recess. In an aspect of the invention, each catch may have a top surface configured to releasably engage the circumferential recess defined in the side surface of the circular hub and a bottom surface and the bottom surface is beveled.

The connector is rotatably coupled to the circular hub on the base of the enteral feeding device. That is, when coupled to the base of the enteral feeding device, the connector may rotate completely about the circular hub in either direction of rotation without inadvertently decoupling from the enteral feeding catheter device or causing the enteral feeding device to twist. Desirably, the connector will provide relatively little resistance to rotation so it may move readily in response to twisting, torquing or other forces to avoid kinking the tube or transferring force to the device.

A conduit may define a fluid pathway through the connector and can be configured to supply a feeding solution to a lumen of the enteral feeding device. The fluid pathway may be spatially positioned between opposed lift tabs. The fluid pathway may define a 90-degree bend such that the fluid pathway has one section that is generally perpendicular to the lumen of the enteral feeding device. Alternatively, the fluid pathway may be configured to have the same orientation as the lumen of the enteral feeding device. Such a configuration is desirable for delivering a bolus of feeding solution. The conduit at the proximal end of the connector may be in the form of a nozzle that is configured to engage a passageway opening defined in the hub to supply a feeding solution through the indwelling catheter of an enteral feeding device. Alternatively, the conduit may be configured to engage a nozzle protruding from the surface of the hub to supply a feeding solution to the indwelling catheter of an enteral feeding device.

The connector may further include motion limiters to limit the pitch and/or roll of the connector (i.e., movements or oscillations about an axis that is parallel to the passageway opening defined in the hub and perpendicular to the upper surface of the hub or the upper surface of the base such that circumferential portions of the connector may move up or down and the opposed circumferential portions of the connector may move oppositely). These motion limiters may be configured to contact an upper surface of the hub or an upper surface of the base of the enteral feeding device.

In an aspect of the invention, the cap may have two slots extending from the circumferential region of the cap towards the central region and these slots define two lobes that both are resilient or have resilient portions. The cap may have three slots extending from the circumferential region of the cap towards the central region and these slots define three lobes with adjacent or opposite lobes having at least one resilient portion in one of the lobes. Additional combinations of slots and lobes are contemplated.

In another aspect of the invention, each lobe may have a port located above the catch to permit visual inspection of engagement between the catch and the circumferential recess defined in the side surface of the circular hub. In another aspect of the invention, each lobe may be reversibly displaced when a force of between about 2 Newtons and about 14 Newtons is applied to its respective lift tab.

The present invention also encompasses an enteral feeding assembly. The enteral feeding assembly is composed of: (i) an enteral feeding device having a base and including at least one indwelling catheter or tube with a lumen positioned through the base, the base having at least one circular hub having a radius, a top surface, a side surface and a circumferential recess defined in the side surface; and (ii) an extension set with a connector as generally described above for rotatably coupling the extension set to the base of the enteral feeding device wherein the connector allows for fluid communication between the extension set and the lumen of the enteral feeding device.

The present invention further encompasses a feeding extension set. The feeding extension set includes a medical fluid supply tube and a connector in fluid communication with the tube, the connector configured for use with an enteral feeding device having a circular hub is a connector as generally described above.

BRIEF DESCRIPTION OF THE DRAWINGS

FIG. 1C is a perspective view illustrating yet another exemplary connector for coupling a feeding extension set to an enteral feeding device having a circular hub. The exemplary connector also has two adjacent lobes as well as a fixed portion.

FIG. 1D is a perspective view illustrating another exemplary connector for coupling a feeding extension set to an enteral feeding device having a circular hub. The exemplary connector has three lobes.

FIG. 2 is perspective view illustrating an exemplary connector of FIG. 1A in position above an enteral feeding device having a circular hub.

FIG. 4A is a perspective view illustrating a detail of an exemplary connector prior to coupling with a feeding extension set to an enteral feeding device having a circular hub.

FIG. 4B is a perspective view illustrating a detail of an exemplary connector coupled with a feeding extension set to an enteral feeding device having a circular hub.

FIG. 5A is a cross-sectional view illustrating a detail of an exemplary connector coupled to the circular hub on the base of the enteral feeding device from FIG. 3, taken along line 5-5.

FIG. 5B is a cross-sectional view illustrating a detail of another exemplary connector.

FIG. 5C is a perspective view illustrating a detail of another exemplary connector.

FIG. 6 is a perspective view illustrating a detail an exemplary connector including a conduit.

FIG. 7 is a cross-sectional view illustrating a detail an exemplary connector including a conduit from FIG. 6, taken along line 7-7.

DETAILED DESCRIPTION

Figure 1B:
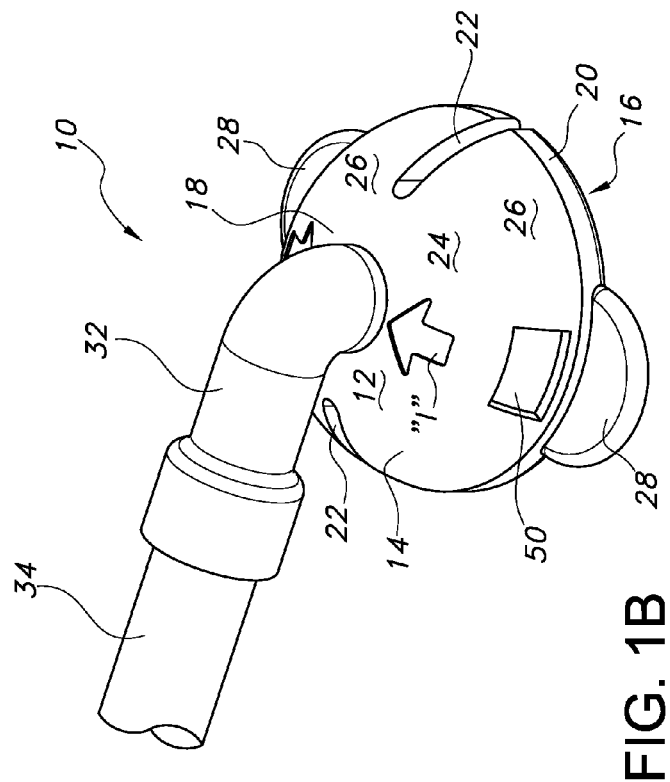
FIG. 1B is a perspective view illustrating another exemplary connector for coupling a feeding extension set to an enteral feeding device having a circular hub. The exemplary connector has two opposing lobes.

Reference will now be made in detail to one or more embodiments, examples of which are illustrated in the drawings. It should be understood that features illustrated or described as part of one embodiment may be used with another embodiment to yield still a further embodiment. It is intended that the claims include these and other modifications and variations as coming within the scope and spirit of the disclosure.

Turning now to the drawings, FIGS. 1A to 1D of the drawings are perspective views illustrating exemplary connectors for coupling a medical fluid supply tube (i.e., the tube) to a base of a catheter device (e.g., an enteral feeding device) having a circular hub. As used herein, the term "fluid" encompasses liquids, gases and combinations thereof. An example of a liquid includes nutritional liquids that may be supplied to a patient through the tube. An example of a gas may be a gas vented from the stomach or intestine of a patient. The connector 10 (which may sometimes be referred to as an "extension set connector" or "feed tube connector" or "tube connector") has a cap 12.

The cap 12 has a top surface 14, a bottom surface 16 a central region 18 and a circumferential region 20. The cap also defines at least two slots 22 that extend from the circumferential region 20 of the cap 12 towards the central region 18. The slots 22 define at least one lobe 26. The lobe(s) 26 is configured to be reversibly displaced via flexing of a resilient material that makes up the lobe or a region of the lobe. As used herein, the term "resilient" refers to the ability of a material to be able to recoil or spring back into shape after bending, stretching, or being compressed. With respect to the present invention, at least the resilient lobe or lobes of the cap are made of a resilient material that can be reversibly displaced. Suitable materials include polyethylene terephthalates, polypropylenes, high and low density polyethylenes, polyurethanes and silicones that are not hard or "brittle". Blends of these materials may be used. These materials desirably form a living hinge or flap that can be readily displaced and which will revert to its original shape or condition.

Figure 1A:
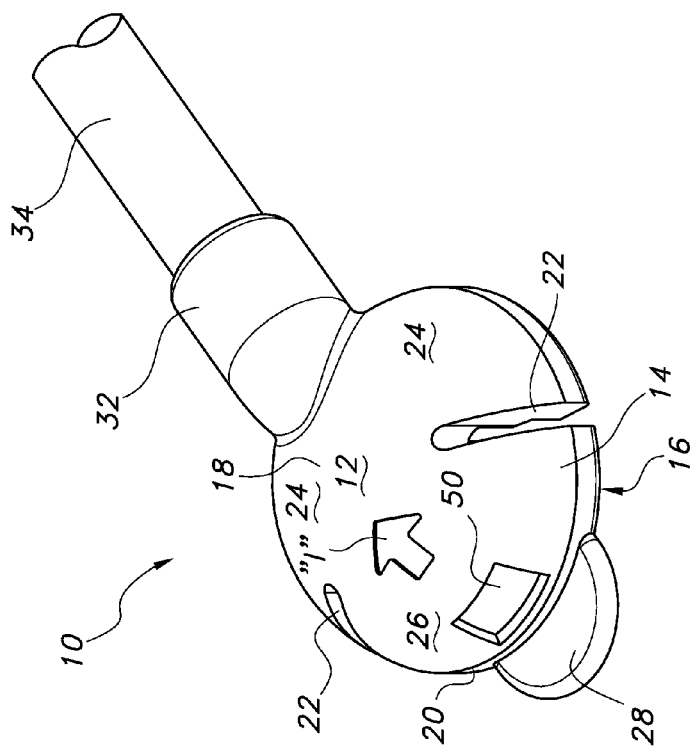
FIG. 1A is a perspective view illustrating an exemplary connector for coupling a feeding extension set to an enteral feeding device having a circular hub. The exemplary connector has one lobe.

FIG. 1A illustrates two slots 22 defining two lobes 26 and the remaining portion 24 of the cap is not a lobe that can be as easily or readily reversibly displaced as the lobe 26. Both lobes 26 can be made of an entirely resilient material. FIG. 1B is a perspective view illustrating an exemplary connector having two slots 22 defining two lobes 26. That is, the lobes 26 can form essentially the entire cap 12 and can be easily or readily reversibly displaced. In other suitable embodiments a lobe may be resilient in one region and non-resilient in another region, e.g. resilient near the circumferential region 20 and less resilient or not resilient towards a central region 18. FIG. 1C is a perspective view illustrating an exemplary connector having three slots 22 defining two lobes 26. That is, the two lobes 26 form a major portion of the entire cap 12 and are easily or readily reversibly displaced and a minor remaining portion 24 of the cap is not as easily or readily reversibly displaced as the lobes 26. FIG. 1D is a perspective view illustrating an exemplary connector having three slots 22 defining three lobes 26. That is, the three lobes 26 form essentially the entire cap 12 and are easily or readily reversibly displaced, e.g. the entire cap and lobes are made of resilient material. It is contemplated that a thin flexible film may cover the cap 12 and the slots 22 or a resilient foam material may fill the slots 22. However, the slots desirably are voids or unbounded openings entirely through the cap 12 and are present to structurally decouple the lobes 26 so the lobes may be reversibly displaced independently of each other.

Each lobe 26 includes a lift tab 28 (which may also be referred to as a projection, tongue, etc.) extending or projecting outwardly (with respect to the cap 12) with respect to the circumferential region 20. Each lobe 26 includes a catch 30 extending or projecting inwardly (with respect to the cap 12) in the circumferential region 20.

The connector may also include a conduit 32 defining a fluid pathway for transferring feeding solution from the tube 34 to the lumen of a device 36.

The exemplary connector 10 of FIG. 1A is shown in FIG. 2 positioned above a device 36 that is equipped with a base 38 having a circular hub 40. The circular hub has a radius "R", a top surface 42, a side surface 44, and a circumferential recess 46 defined in the side surface 44. In other words, the circular hub 40 has a generally horizontal top surface 42 that extends over a generally vertical side surface 44 forming rim, collar, rib or flange structure 48 that defines a circumferential recess 46 which is sized to engage the catches 30 of the connector 10. The radius "R" is the distance from the center of the hub 40 to the outermost edge "E" of the portion of the top surface 42 forming the rim, collar, rib or flange structure 48 that defines the recess 46. The circular hub 40 also includes a passageway opening or orifice "O" at the center of the hub. A valve "V" is desirably used to seal the orifice "O" when the connector 10 is not engaged with the circular hub 40.

Generally speaking, the catch 30 is configured to releasably engage the circumferential recess 46 defined in the side surface 44 of the circular hub 40. The connector 10 is coupled to the circular hub 40 by positioning the connector 10 on the circular hub 40 and pressing the connector onto the hub until the catches engage the circumferential recess defined in the side surface of the circular hub. The catches 30 may be seen in more detail in FIG. 9 which is a bottom view of the connector of FIG. 1A. In this particular connector, one of the catches 30 is located on the lobe 26 and one of the catches 30 is located on the fixed portion 24 of the cap 12. It is contemplated that more than one catch may be located on lobe 26 and/or the fixed portion 24 of the cap 12. For the connector illustrated in FIG. 1A and FIG. 9, depressing the connector causes the lobe 26 to move via flexible or deformation of the resilient region(s) until both of the catches engage the circumferential recess defined in the side surface of the circular hub. This may cause a slight horizontal shifting or displacement of cap as the catch 30 on the fixed portion 24 of the cap clears the outermost edge "E" of the top surface 42 forming the rim, collar, rib or flange structure 48, seating the connector 10 on the circular hub 40. Of course, the connector 10 may be coupled to the circular hub 40 by squeezing or lifting the lift tab 28 to deform the resilient region of the lobe 26 so the catch 30 on the lobe 26 is well clear the outermost edge "E" of the top surface 42 forming the rim, collar, rib or flange structure 48, and then seating the connector 10 on the circular hub 40 and releasing the squeezing or lifting force on the lift tabs 28 so the catches 30 engage the circumferential recess 46. The catches 30 are configured to releasably engage an underside (not shown) of the generally horizontal top surface 40 that extends over the generally vertical side surface 42 forming rim, collar, rib or flange structure 48 that defines the circumferential recess 46.

With respect to the connectors illustrated in FIGS. 1B to 1D, the catches 30 may be positioned exclusively on the lobes 26. However, it is contemplated that some of the catches may also be positioned on fixed portions 24 of the cap (where/when fixed portions may be present) that are not lobes provided that the positioning of the catches on the fixed portions of the cap does not interfere with the coupling of the connector to the circular hub. When catches are positioned on the fixed portions of the cap, these catches should be located on a portion of the cap opposite from the lobes so that the connector may be coupled with the circular hub 40 by positioning the connector 10 on the circular hub 40 and depressing the connector until the catches engage the circumferential recess defined in the side surface of the circular hub. The lobes 26 of cap 12 readily deflect as the downward pressure or force is applied to the connector allowing the catches 30 to slide past the edge "E" of the top surface 42 forming the rim, collar, rib or flange structure 48 on the circular hub 40. The catches 30 engages in the circumferential recess 46 defined in the side surface 44 of the circular hub 40 to couple the connector to the circular hub 40 on the base 38 of an enteral feeding device 36. The catches 30 are configured to releasably engage an underside (not shown) of the generally horizontal top surface 40 that extends over the generally vertical side surface 42 forming rim, collar, rib or flange structure 48 that defines the circumferential recess 46.

Figure 9:
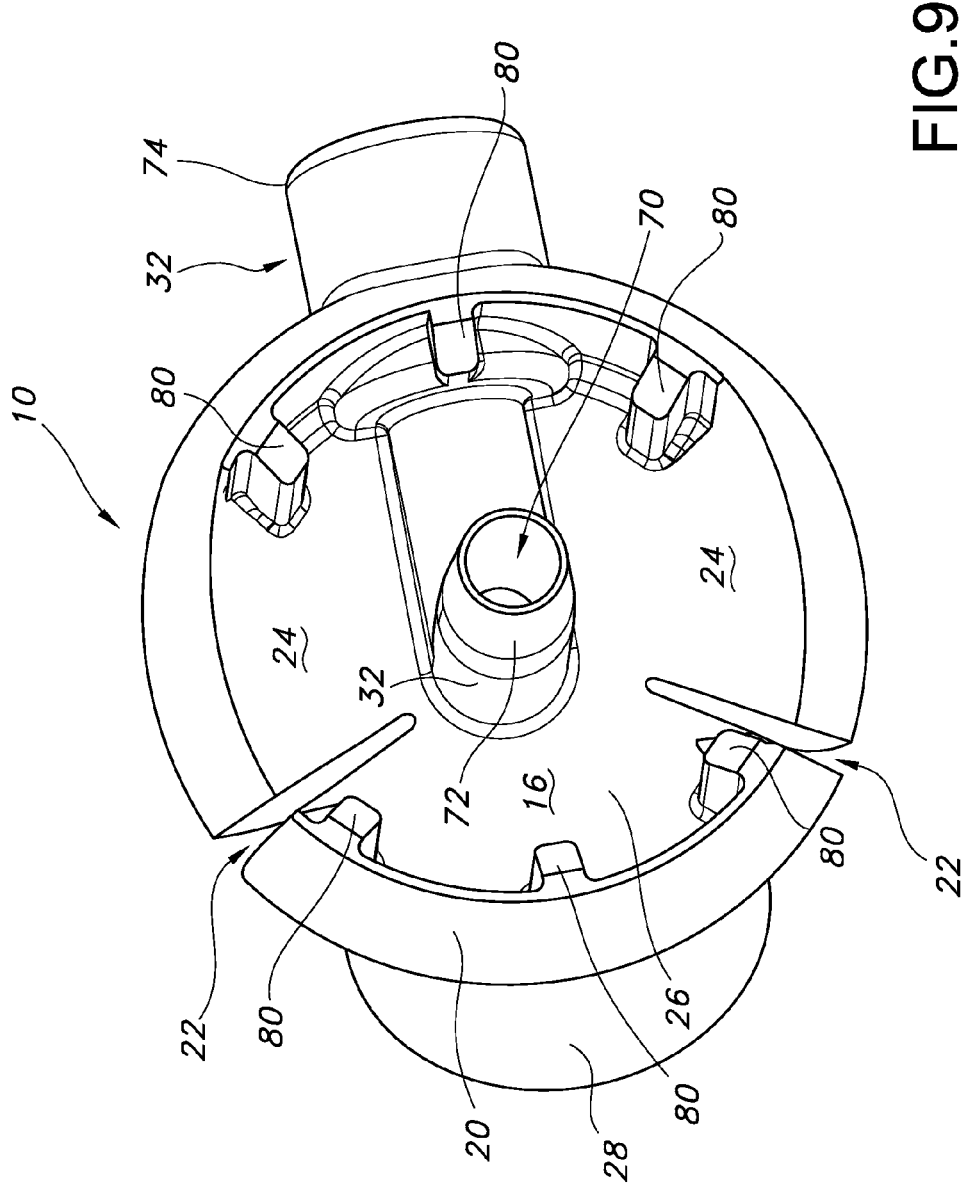
FIG. 9 is a bottom view of an exemplary connector from FIG. 1A.

The connector illustrated in FIG. 1A and FIG. 9 is decoupled from the hub by lifting the lift tab(s) 28 to reversibly displace the lobe(s) 26 and its associated catch 30 radially (e.g., radially outward) to disengage from the circumferential recess 46. A slight horizontal shifting or displacement of cap may be required as the catch 30 on the fixed portion 24 of the cap clears the outermost edge "E" of the top surface 42 forming the rim, collar, rib or flange structure 48 to disengage the connector 10 on the circular hub 40. With respect to the connectors illustrated in FIGS. 1B to 1D, these connectors may be decoupled from the circular hub 40 by lifting the lift tabs 28 to reversibly displace the respective catches 30 radially outward to disengage from the circumferential recess 46. That is, the catches 30 may desirably be located only on the lobes. When the lift tabs 28 are lifted or biased upwardly, the lobes 26 are reversibly displaced via deformation of their resilient regions to move the respective catches 30 radially outward away from the circular hub 40 to disengage from the circumferential recess 46 defined in the side surface 44 of the circular hub 40. In those instances where the connectors illustrated in FIGS. 1B to 1D have one or more catches also located on a fixed portion 24 of the cap, a slight horizontal shifting or displacement of cap may be required as the catch 30 on the fixed portion 24 of the cap clears the outermost edge "E" of the top surface 42 forming the rim, collar, rib or flange structure 48 to disengage the connector 10 on the circular hub 40. In an aspect of the invention, each lobe may be made to include at least a region of a resilient material such that it is reversibly displaced by a force of between about 2 and about 14 Newtons applied to its respective lift tab. Exemplary materials include, polyethylene terephthalates, polypropylenes, high and low density polyethylenes, polyurethanes and silicones that are not hard or "brittle" and combinations/blends thereof. It is contemplated that the lobe may have regions that are thinner than the other portions of the cap. It is also contemplated that the lobe may have a graduated thickness or varying levels of thickness to enhance its resilient characteristics or to control the extent and/or location of resiliency such that it is reversibly deformable. A feature of the present invention is that the lobe is resilient and is reversiblely deformable to engage and disengage the cap. By manipulating the resilience of the lobe(s) of the cap (rather than requiring the entire cap to be resilient), it is thought that the force needed to engage and disengage the connector from the circular hub can be more carefully controlled to avoid transferring force to a patient which may cause irritation (e.g., of a stoma site) and to allow secure connection/disconnection without requiring an undesirably high level of force.

Desirably, the connector is rotatably coupled to the circular hub on the base of the device. That is, the connector may rotate completely about the circular hub in either direction of rotation without disconnecting from the device or causing the device to twist. It is desirable for the connector to be rotatably coupled such that it can rotate freely around the circular hub with relatively little resistance. Also shown in FIG. 2 is a port or opening 50 in the lobe 26 located above the catch to permit visual inspection of engagement between the catch 30 and the circumferential recess 46 defined in the side surface 44 of the circular hub 40.

Figure 3:
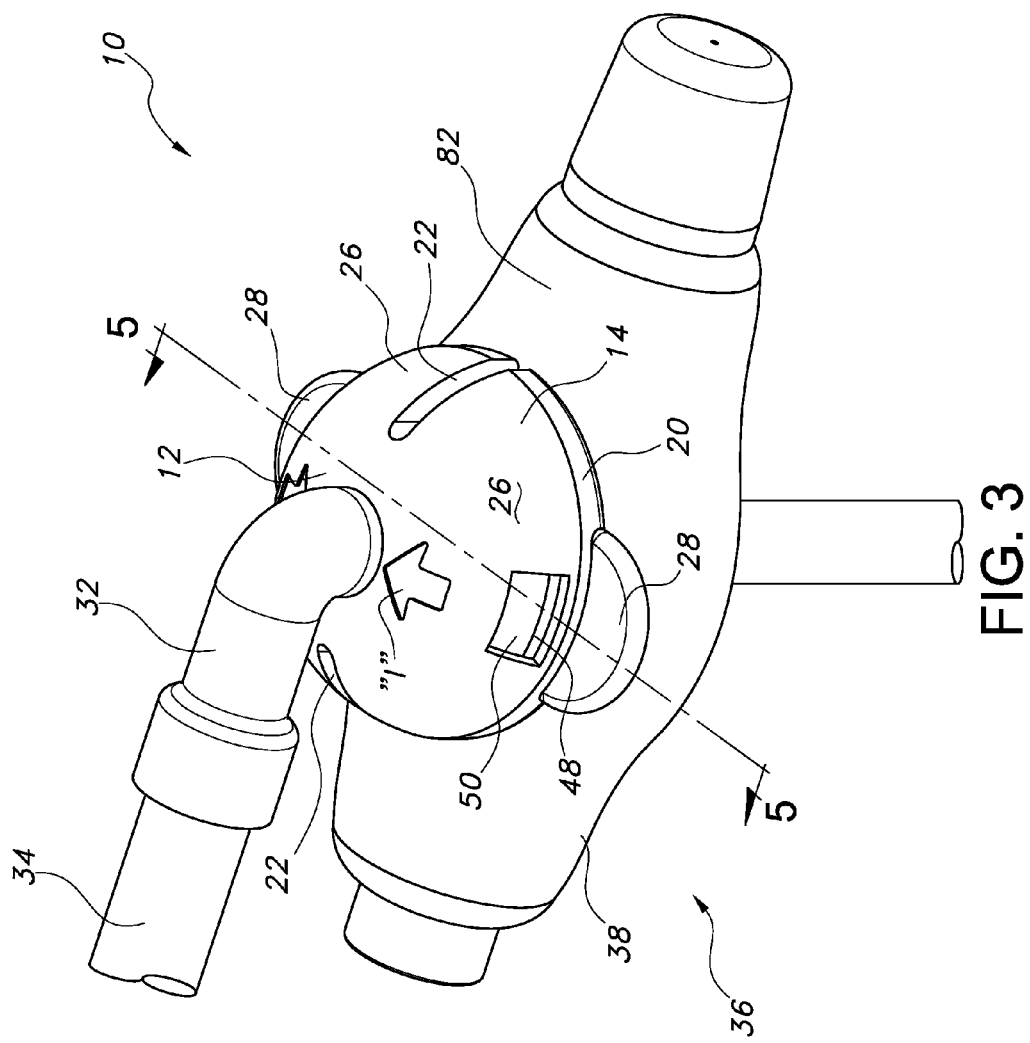
FIG. 3 is perspective view illustrating an exemplary connector of FIG. 1B coupled to the circular hub on the base of the enteral feeding device.

Referring now to FIG. 3 of the drawings, there is shown in perspective view an illustration of the connector 10 from FIG. 1B coupled with a device 36. Illustrated in this view is the optional port 50 that allows visual inspection of the inspection of engagement between the catch 30 and the circumferential recess 46 defined in the side surface 44 of the circular hub 40. More particularly, the outermost edge of the rim, collar, rib or flange structure 48 is visible through the port 50. This is illustrated in more detail in FIGS. 4A and 4B which are top perspective views of the cap 12 highlighting the port 50 in the lobe 26. Referring to FIG. 4A, a portion of the catch 30 may be seen through the port 50 prior to coupling the connector 10 with the device. As illustrated in FIG. 4B, after coupling the connector 10 with the device, the outermost edge of the rim, collar, rib or flange structure 48 is visible through the port 50 indicating engagement between the connector 10 and the device 36.

Referring now to FIG. 5A of the drawings, there is shown in side cross-sectional view, an illustration of details from the connector 10 of FIG. 3, taken along line 6-6, coupled with the device 36. In this view, the cap 12 contacts the circular hub 40. A defined fluid pathway 70 may pass through conduit 32 of the connector 10. As can be seen in FIG. 5A, the optional port 50 allows visual inspection of the inspection of engagement between the catch 30 and the circumferential recess 46 defined in the side surface 44 of the circular hub 40. More particularly, the outermost edge of the rim, collar, rib or flange structure 48 is visible through the port 50. In addition, the connector 10 may further include motion limiters 80 to limit the pitch of the connector. More particularly, the cross-sectional view of FIG. 5 illustrates a pair of motion limiters 80 integrated with or joined to part of the cap 12 and configured to contact an upper surface of the hub 24. It is contemplated that the cap 12 and motion limiters 80 may be configured so the motion limiters 80 may contact an upper surface 82 of the base 38 of the device 36. Alternatively and/or additionally, the motion limiters 80 may constitute a portion of the conduit 32 or, more desirably, may constitute part of the fixed portion 24.

The lift tab 28 may have topography to help the users identify the lift tab 28 through visual and/or tactile indicia such as, for example, bands, bumps, ridges, raised dots, random rough texture, contracting color or the like. Alternatively and/or additionally, the cap 12 of the connector 10 may include indicia "I" as illustrated in FIGS. 1A, 1B, 1C, 1D as well as FIGS. 2, 3, and 6. These indicia "I" may be used to provide a tactile or visual cue to a user about the location of the release buttons and/or the direction to press squeeze or pinch the lift tabs.

FIG. 5B is an illustration of details from an exemplary connector shown in side cross-sectional view. FIG. 5B illustrates an alternative lift tab 28 configuration in which lift tabs are on opposed portions of the cap 12 of the connector 10. In this configuration, the lift tabs 28 in a generally perpendicular arrangement to the orientation of the catch 30 such that squeezing the lift tabs 28 is translated to rotational movement via deformation and displacement of the lobe 26 to move the catches 30 radially outward to disengage from the recess 46 in the circular hub 40. FIG. 5C is an illustration of yet another exemplary connector in perspective view highlighting a lift tab 28 in a generally perpendicular arrangement to the orientation of the catch 30 such that squeezing the lift tab 28 is translated to rotational movement via deformation and displacement of the lobe 26 to move the catch 30 radially outward to disengage from the recess 46 in the circular hub 40.

Figure 10:
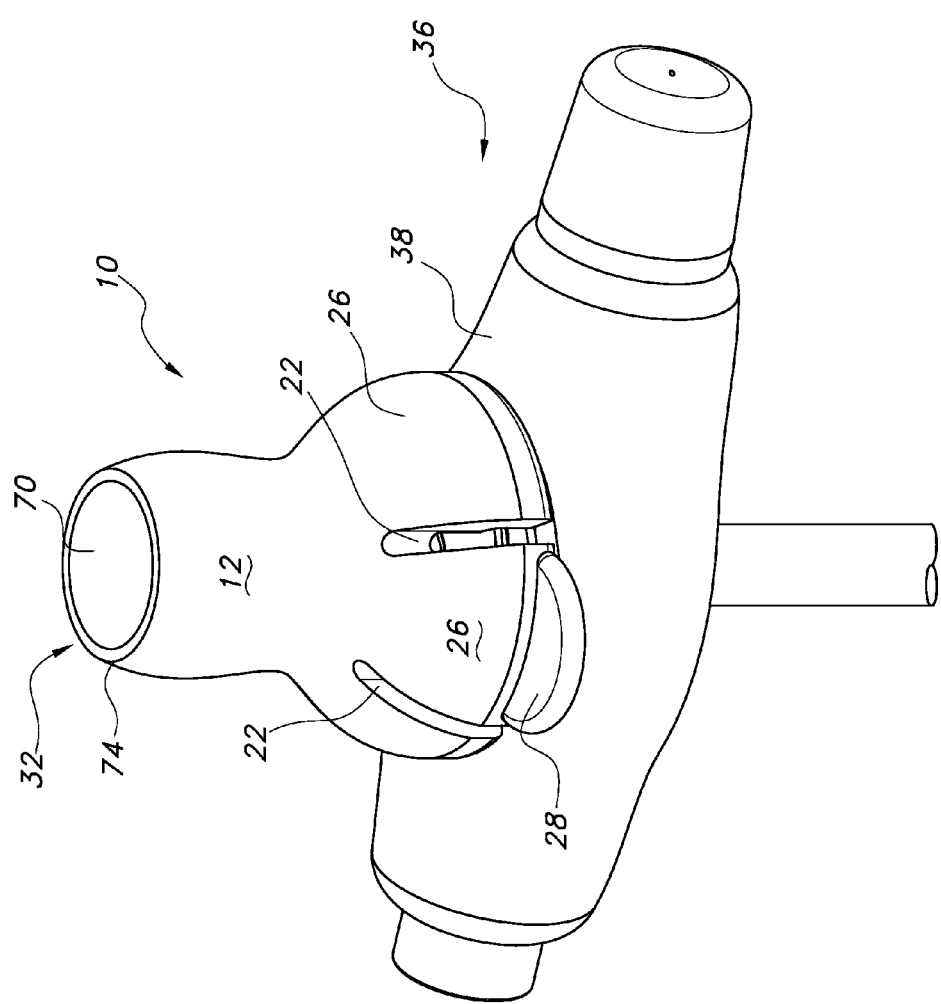
FIG. 10 is a side perspective view illustrating an exemplary connector in which both a proximal end and a distal end of a conduit defining a fluid pathway are axially aligned with the lumen of an enteral feeding device and engaged with the base of the enteral feeding device.

Referring now to FIGS. 6 and 7, FIG. 6 shows a perspective view of a connector 10 including a conduit 32 defining a fluid pathway 70 through the connector and FIG. 7 shows a cross-sectional view of the connector 10 from FIG. 6, taken along line 7-7, including a conduit 32 defining a fluid pathway 70 through the connector. The conduit 32 is configured to supply a feeding solution from tube 34 to a lumen of device 36. A proximal end 72 of the conduit 32 defining the fluid pathway may be axially aligned with the lumen of device and then may have a 90 degree bend such that a distal end 74 of the conduit 32 extends in a generally perpendicular manner to proximal end 72. This configuration is useful for most feeding applications. Alternatively, the proximal end 72 of the conduit 32 defining the fluid pathway 70 may be axially aligned with the lumen of the enteral feeding device and then may continue such that the distal end 74 of the conduit 70 continues to extend in an axially aligned manner to the proximal end. Such a configuration is illustrated in side perspective view in FIG. 10, which shows the extension set connector 10 coupled with the base 38 of an enteral feeding device 36. Such a configuration is desirable for delivery of a bolus of feeding solution.

The conduit 30 may be in the form of a nozzle as generally illustrated in FIGS. 1A, 1B, 10, 1D, 2, 5, 6 and 7 that is configured to extend beyond a plane defined by the bottom surfaces the lift tabs 28 of the connector to engage an orifice "O" defined in the hub 40 to supply a feeding solution to a lumen (defined by the indwelling catheter of the device. Alternatively, the conduit 32 may be configured to engage a nozzle (not shown) protruding from the top surface of the hub to supply a feeding solution.

Generally speaking, the connector 10 is positioned directly over the circular hub 40 for coupling. As the connector is depressed onto the circular hub, the connector contacts these regions of the circular hub to couple the connector to the circular hub 40: top surface 42, edge E, flange structure 48, and circumferential recess 46. The lobes 26 of cap 12 readily deflect as downward force is applied to the connector and the catches 30 slide past the upper edge "E" of the rim or flange structure 48 on the circular hub 40 (as shown in FIG. 2 and FIG. 5). The catches 30 engage the circumferential recess 46 defined in the side surface 44 of the circular hub 40. The catches 30 are configured to releasably engage an underside (not shown) of the generally horizontal top surface 42 that extends over the generally vertical side surface 44 forming rim, collar, rib or flange structure 48 that defines the circumferential recess 46.

The downward force needed to accomplish the coupling is generally less than about 10 Newtons and is desirably between about 0.1 Newtons and 8 Newtons. Such a low level of force is very important because the downward force is transferred directly to the enteral feeding device which resides in the sensitive stoma site. This configuration avoids the much higher levels of forces that are required to couple a snap-type connector into place. Unlike such 'high force' coupling connectors, the invention avoids irritating the sensitive stoma site; the low level of force used to engage the connector helps patients that are mobility impaired, sight impaired, or who otherwise have difficulty seeing or reaching the device (e.g., obese patients, patients with poor motor skills, etc.).

The lobes 26 and the catches 30 on at least those lobes (as well as catches that may be on the fixed portions) also provide a positive tactile signal when the catches 30 slide into the circumferential recess 46 defined in the side surface 44 of the hub. The lobes 26 may transmit a feeling of increasing resistance as they progressively slide against top surface 42 and radially deflect towards and around the dimensions defined by edge "E" as the connector is pressed onto the hub. Such resistance immediately dissipates when the catches enter the recess to provide a tactile signal. This action may also produce an audible signal that may be characterized as a "snap" or "click" to alert the user that the catches are correctly positioned in the recess. These tactile and audible signals help communicate to users and care providers that a proper and secure connection is made.

According to the invention, the connector 10 decouples from the circular hub 40 by lifting the lift tabs 28 to reversibly displace the respective catches 30 radially outward to disengage from the circumferential recess 46. When the lift tabs 28 are lifted or biased upwardly, the lobes 26 spatially move the respective catches 30 radially outward and away from the circular hub 40 so that they are at or clear the edge "E". The displacement of the catches 30 results from the flexing or deformation of the resilient regions of lobes 28. For example, each lobe may be made of a material such that the lobe takes on a changed, but reversible, spatial configuration when its respective lift tab is subjected to a force of between about 2 and about 14 Newtons.

Figure 8:
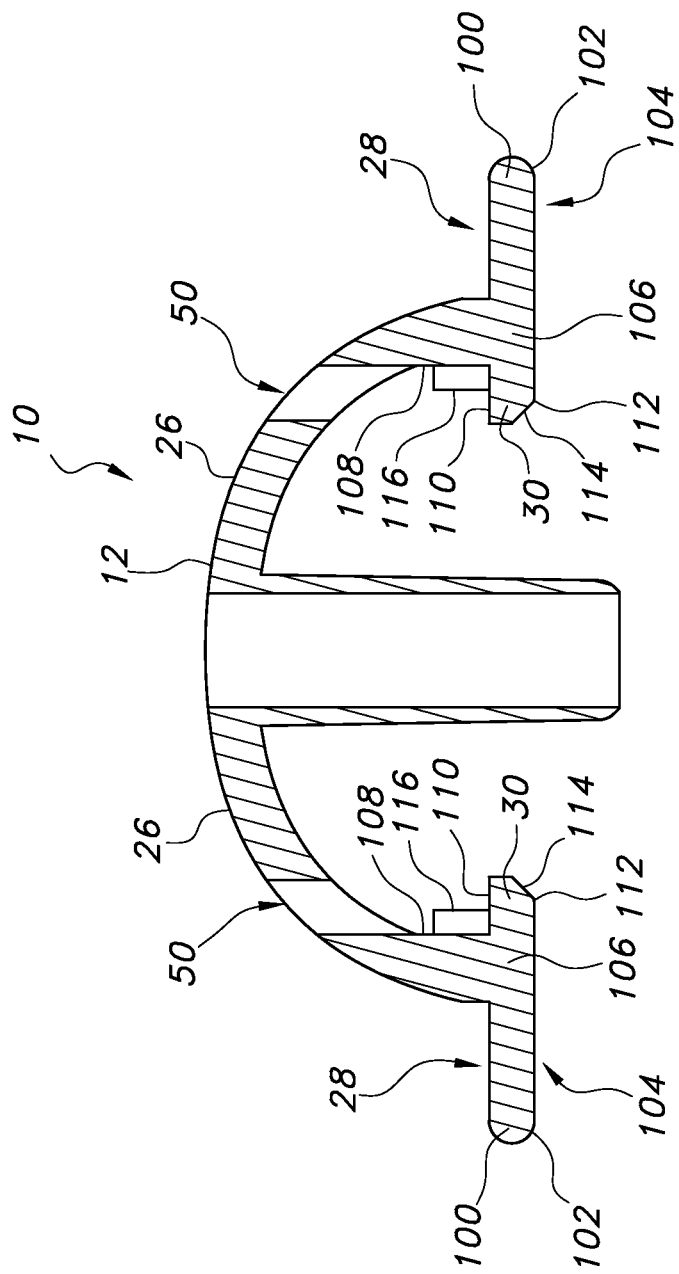
FIG. 8 is a side cross-sectional view illustrating a detail of a portion of an exemplary connector.

Referring now to FIG. 8, there is shown in side cross-sectional view an illustration which highlights exemplary details of a lobe 26. Each lift tab 28 has a first portion 100 with an exterior, outer or outward facing surface 102 that forms or includes a finger contact zone 104. In addition, each lift tab 28 has a second portion 106 with an interior, inner or inward facing surface 108 that forms or includes a catch 30. The catch 30 is configured to releasably engage the circumferential recess defined in the side surface of the circular hub. Desirably, each catch 30 may have a top surface 110. The top surface 110 is configured to lie adjacent an underside (not shown) of rim, rib or flange structure 48 that defines the circumferential recess 46. Each catch may also have a bottom surface 112. Desirably, a portion of the bottom surface 112 may have a bevel 114. The bevel 114 can be adjusted to provide an angle sufficient to allow for easier attachment when the connector 10 is pressed downward against and onto the circular hub 40. The presence of the bevel 114 helps avoid applying a force that creates discomfort and causes irritation to the sensitive stoma site. The second portion 106 of the lift tab 28 may further include an optional boss 116 adjacent the catch 30. The purpose of the boss 116 is to slightly displace the lobe 26 when the connector 10 is coupled to the base 38. This displacement provides a tension or load to the lobe 26 that is transferred to the catches 30 to secure the connector 10 to the circular hub so it does not wobble or rattle, yet is able to rotate in response to a relatively low level of force.

As noted above, the connector includes cap 12. The cap 12 may have a clamshell or bowl shape. The cap 12 may be formed as a unitary element such that the lobes 26 (and any optional fixed or non-resilient portions or lobes 24) are unitary or monolithic. In an aspect of the invention, the lift tabs 28 and the catches 30 may be joined to the lobes or, more desirably, they may be formed as one piece with the lobes 26 or, more desirably, as one piece with the lobes 26 and the fixed lobes 24 (i.e., the cap 12). Alternatively, all the various structural members of cap 12 may be formed separately and subsequently joined together by techniques involving adhesion, fusion, overmolding, etc. alone or in combination.

Referring now to FIG. 9, there is shown a bottom view of an exemplary connector 10 from FIG. 1A illustrating the bottom surface 16 of the cap 12. In this illustration, optional motion stabilizers 80 are located along the circumferential region 20 of the cap 12. As can be seen in FIG. 9, a catch 30 is located on lobe 26 and a catch 30 is on the fixed portion 24 of the cap 12 directly opposite lobe 26. In FIG. 9, the ports 50 are not illustrated.

According to the invention, the connector 10 is "rotatably coupled" to the circular hub 40. That is, the connector freely rotates completely about the circular hub when coupled to the base of the device. The connector is configured to freely rotate completely around the hub without passing through a position or location where the connector encounters a feature such as a keyway, a groove, a slot or the like which would allow the connector to be inadvertently disengaged and/or without encountering a feature such as a stop, detent or the like that would inhibit or prevent rotation completely around the hub thereby causing the device to twist. Desirably, the connector is configured to rotate completely around the hub multiple times while providing little or no resistance so that the enteral feeding device does not twist or turn.

The present invention also encompasses an enteral feeding assembly. The enteral feeding assembly is composed of: (i) an enteral feeding device having a base and including a catheter with a lumen positioned through the base, the base having a circular hub having a radius, a top surface, a side surface and a circumferential recess defined in the side surface; and (ii) an extension set with a connector for rotatably coupling to the base of the enteral feeding device. The connector is as generally described above.

The present invention further encompasses a feeding extension set. The feeding extension set includes a medical supply tube and a connector for use with an enteral feeding device having a circular hub. The connector is as generally described above.

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

We claim:

1. A connector for coupling a medical fluid supply tube to the head of a catheter device having a circular hub with a circumferential recess defined in a side surface of the circular hub, the connector comprising:

a cap having a top surface, a bottom surface, a central region, and a circumferential region radially inward of a circumferential edge;

the cap defining at least two slots, each slot defined completely through the cap and extending through the circumferential edge of the cap towards the central region, the slots defining at least one lobe with a radially extending space in the cap along each side of the lobe and through the circumferential edge, the at least one lobe including:

a lift tab extending radjally outward beyond the circumferential edge of the cap, an inwardly projecting catch that is configured to releasably engage the circumferential recess, and at least a resilient region;

wherein the connector is free to rotate completely about the circular hub, and wherein the connector decouples from the circular hub by actuating the lift tab to reversibly displace the lobe and its respective catch radially by deforming the resilient region, in order to disengage the catch from the circumferential recess without displacing the circumferential edges of the cap adjacent to the lobe.

2. The connection of claim 1, wherein the connector is coupled to the hub by positioning the connector on the hub and pressing the top surface of the cap to move the bottom surface of the cap towards the hub until the catches engage the circumferential recess.

3. The connector of claim 1, wherein the at least one lobe is reversibly deformed and spatially displaced when a force of between about 2 Newtons and about 14 Newtons is applied to its respective lift tab.

4. The connector of claim 1, further comprising motion limiters to limit the pitch of the connector.

5. The connector of claim 1, wherein each catch has a top surface configured to releasably engage the circumferential recess defined in the side surface of the circular hub and a bottom surface that is beveled.

6. The connector of claim 1, further comprising a conduit defining a fluid pathway through the connector, the conduit configured to supply a liquid to a lumen defined by a catheter of the device.

7. The connector of claim 1, wherein the cap comprises two slots extending from the circumferential region of the cap towards the central region and the slots define two lobes.

8. The connector of claim 1, wherein the cap comprises three slots extending from the circumferential region of the cap towards the central region and the slots to define three lobes.

9. The connector as in claim 1, wherein the catheter device is an enteral feeding device having a circular hub, the connector configured to connect the medical supply tube to the circular hub of the enteral feeding device.

10. The connector as in claim 9, further comprising an enteral feeding extension tube in fluid communication with the connector.

11. A connector for coupling a medical fluid supply tube to the head of a catheter device having a circular hub with a circumferential recess defined in a side surface of the circular hub, the connector comprising:
- a cap having a top surface, a bottom surface, a central region, and a circumferential region;
- the cap defining at least two slots, each slot extending from the circumferential region of the cap towards the central region, the slots defining at least one lobe, the at least one lobe including:
  - an outwardly projecting lift tab,
  - an inwardly projecting catch that is configured to releasably engage the circumferential recess, and
  - at least a resilient region;
- wherein the connector is free to rotate completely about the circular hub, and wherein the connector decouples from the circular hub by lifting at least one lift tab to reversibly displace the lobe and its respective catch radially by deforming the resilient region, in order to disengage from the circumferential recess; and
- wherein the at least one lobe has a port located above the catch to permit visual inspection of engagement between the catch and the circumferential recess defined in the side surface of the circular hub.

* * * * *